United States Patent [19]

Carmeli

[11] Patent Number: 5,063,163

[45] Date of Patent: Nov. 5, 1991

[54] METHOD OF DETECTING COUNTERFEIT PAPER CURRENCY

[75] Inventor: Dov Carmeli, Tampa, Fla.

[73] Assignee: Ach Group, Inc., Tampa, Fla.

[21] Appl. No.: 496,349

[22] Filed: Mar. 20, 1990

[51] Int. Cl.[5] ...................... G01N 33/10; G01N 33/34

[52] U.S. Cl. ...................................... 436/94; 162/140; 162/198; 422/61; 436/164

[58] Field of Search .................. 436/94, 164; 162/149, 162/198; 422/61

[56] References Cited

PUBLICATIONS

Casey, "Pulp and Paper Chemistry and Chemical Technology", 3rd vol. III, 1981.

*Primary Examiner*—Robert J. Warden
*Assistant Examiner*—Lyle A. Alexander
*Attorney, Agent, or Firm*—Shlesinger, Arkwright, Garvey

[57] ABSTRACT

A method of detecting counterfeit paper currency includes applying a test solution having an initial color to an area of a paper currency to be tested. After waiting for a predetermined time period, the color of the test area is compared with a predetermined standard to determine if a reaction has taken place, whereby on the application of the test solution to a counterfeit paper currency the net result will be a color change from its initial color to a black coloration and for a genuine paper currency there will be no immediate change in its initial color.

16 Claims, 2 Drawing Sheets

METHOD OF DETECTING COUNTERFEIT PAPER CURRENCY

FIELD AND HISTORICAL BACKGROUND OF THE INVENTION

The present invention is directed to a method of detecting counterfeit paper currency.

Ever since the paper currency was invented and put into use, the governments throughout the world have been concerned with the problem of counterfeiting. As the duplicating and printing, and especially the photocopying technologies have advanced over the years, it is more difficult than ever to distinguish between a counterfeit and a legitimate paper currency. The problem of counterfeiting paper currency is and has been a major concern of many governments around the world.

In response to the ever-growing concern of counterfeiting, devices have been developed for detecting counterfeit currency. However, conventional devices are not reliable, expensive to manufacture, and in some cases, are rather bulky and complex in design.

Therefore, there is a need in the art for a simple method of detecting counterfeit currency.

OBJECTS AND SUMMARY OF THE INVENTION

The principal object of the present invention is to provide a method of detecting counterfeit paper currency which is reliable and does not require the use of expensive, bulky and complex equipment and procedure.

Another object of the present invention is to provide a method of detecting counterfeit paper currency which is fast and easy to implement.

Yet another object of the present invention is to provide a method of detecting counterfeit paper currency which uses a test solution that is easy and inexpensive to manufacture, and can be dispensed in small quantities in containers of simple design and construction.

An additional object of the present invention is to provide a method of detecting counterfeit paper currency that uses a test solution which is made of readily available chemical components.

Yet an additional object of the present invention is to provide a method of detecting counterfeit paper currency which, initially produces a fast and reliable result, and then a final confirmatory result.

In summary, the main object of the present invention is to provide a reliable method of detecting counterfeit paper currency which produces fast results and does not require the use of expensive and complex equipment.

BRIEF DESCRIPTION OF THE DRAWINGS

The above and other objects and advantages and novel features of the present invention will become apparent from the following detailed description of the preferred embodiment of the invention illustrated in the accompanying drawings, wherein.

DETAILED DESCRIPTION OF THE INVENTION

The unique method of the present invention for detecting counterfeit paper currency generally includes applying a test solution which detects the content of starch in the currency paper. The solution, which is light golden-brown in color, when applied to a counterfeit paper currency, forms a bluish-black complex with starch. On the other hand, the color of the test solution does not change in the case of a genuine paper currency, perhaps due to the absence of the counterpart starch molecules required for forming the bluish-black complex.

The test solution is a reagent solution containing iodine and a suitable solvent, preferably selected from the group consisting of alcohol, carbon disulfide, chloroform, ether, carbon tetrachloride, glycerol, and an alkaline iodide solution. The alkaline iodide may preferably be selected from the group consisting of sodium iodide and potassium iodide. In particular, the light golden-brown test solution contains about 0.5% to about 2.0% iodine, about 48.0% to about 49.5% water, and about 44% to about 50% alcohol by volume of the reagent solution. The solution may also contain upto about 6% of a bleaching agent, such as hydrogen peroxide, by volume of the solution. It should be noted that various percentages of the noted ingredients may be altered in order to provide various test solutions of varying strengths. The main component of the test solution is the iodine element and, therefore, other types of reagents may also be used than those listed herein order to produce an iodine solution for use in the method of this invention.

Figure 1:
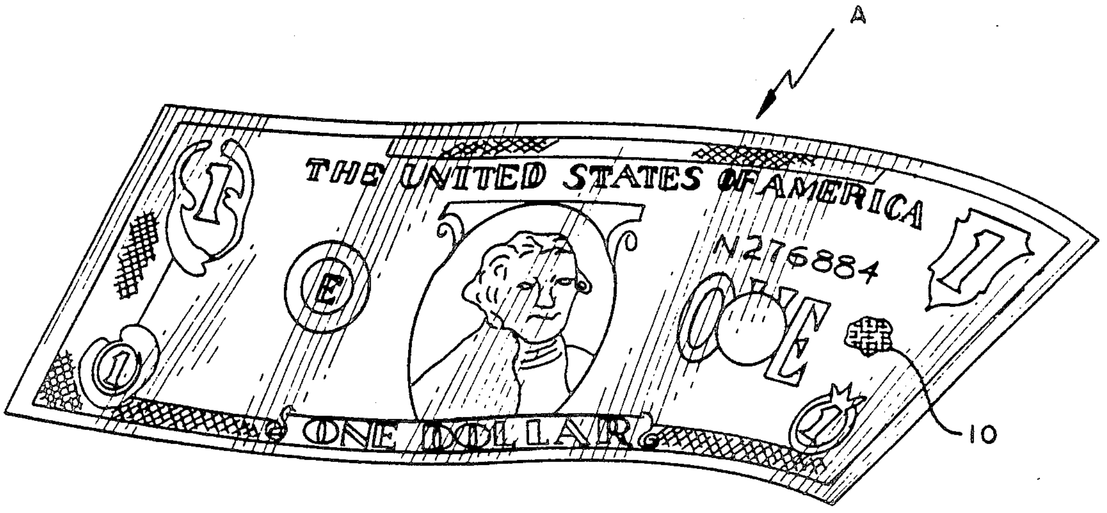
FIG. 1 shows a genuine paper currency with a light golden brown test area.
Figure 2:
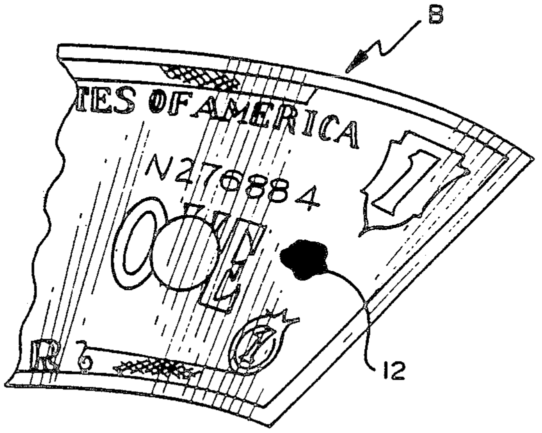
FIG. 2 shows a portion of a counterfeit paper currency with a black colored test area.
Figure 3:
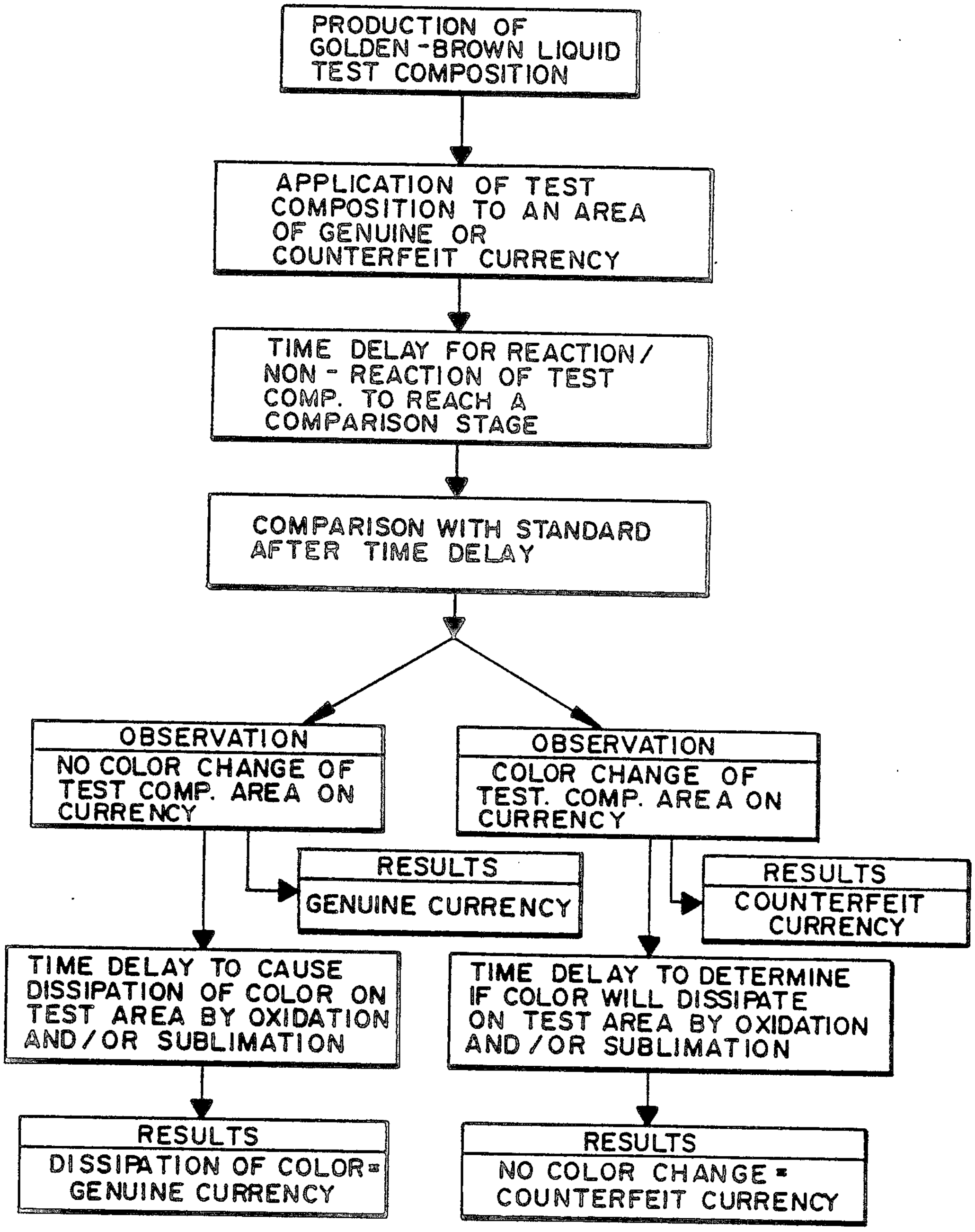
FIG. 3 is a flow chart of the method in accordance with the present invention.

As shown in FIG. 3, the method includes applying the test solution to a paper currency and after a short time delay, i.e., almost immediately to a few seconds, the color of the test area is compared with a predetermined standard (defined below). If the currency is a genuine paper currency (FIG. 1), no color change of the test solution area 10 on paper currency A will be observed. On the other hand, in the case of a counterfeit currency (FIG. 2), the color of the test composition area 12 on the paper currency B will change from light golden-brown to bluish-black or substantially black.

It is believed that the iodine in the test solution reacts with the starch content in the counterfeit paper currency B to form a bluish-black or substantially black complex. On the other hand, the genuine paper currency, either does not contain any starch or its content is chemically untraceable, and therefore, iodine in the test solution remains unreacted and no color change is observed. Therefore, upon application of the solution of the present invention to a paper currency, a light golden-brown colored test area will indicate the presence of a genuine paper currency, and in the case of a counterfeit paper currency, a color change from light golden-brown to bluish-black or substantially black in the test area will be observed.

In order to further confirm the presence or absence of counterfeit currency, the color of the test solution area on the currency may further be observed after another time delay the duration of which would depend upon the strength of the solution, but preferably would be in the range of several hours to a few days. As one of ordinary skill in the art would be aware that iodine is readily sublimed. Therefore, in the case of genuine paper currency A, the light golden-brown colored test area 10 will dissipate due to iodine sublimation, and/or oxidation, if hydrogen peroxide is also included in the solution. However, in the case of counterfeit paper currency B, the bluish-black or substantially black colored test area 12 on the currency will not dissipate.

The test solution can be dispensed in small quantities in containers of varying sizes, and can be applied by any known method, such as by using a dropper or the like device. Alternatively, the solution may also be dispensed in the reservoirs of pen-like writing instruments for quick and easy application. Other suitable methods/devices may also be employed for dispensing and easy application of the test solution.

While this invention has been described as having a preferred method/design, it is understood that it is capable of further modifications, uses and/or adaptations of the invention and following in general the principles of the invention and including such departures from the present disclosure as come within known or customary practice in the art to which the present invention pertains, and as may be applied to central features hereinbefore set forth, and fall within the scope of the invention or the limits of the claims appended hereto.

What I claim is:

1. A method of determining illegitimate paper currency by detecting the starch content therein in excess of the genuine currency, comprising the steps of:

(a) providing a paper currency to be tested;
(b) providing a test solution including iodine and having an initial color;
(c) applying said test solution to an area of said paper currency;
(d) waiting for a predetermined time period; and
(e) comparing the color of said area of said paper currency with a predetermined standard to determine if a reaction has taken place;
(f) whereby on the application of said test solution to a counterfeit paper currency the net result will be a color change from its initial color to a black coloration due to the reaction with starch in the counterfeit paper currency and for a genuine paper currency there will be no immediate change in its initial color.

2. The method of claim 1, comprising the steps of:

(a) providing a test solution containing iodine and hydrogen peroxide.

3. The method of claim 1, comprising the step of:

(a) providing a test solution containing iodine and a solvent selected from the group consisting of alcohol, carbon disulfide, chloroform, ether, carbon tetrachloride, glycerol and an alkaline iodide solution.

4. The method of claim 1, comprising the step of:

(a) providing a test solution containing iodine, an iodide selected from the group consisting of sodium iodide and potassium iodide, and alcohol.

5. The method of claim 1, comprising the steps of:

a) providing a test solution containing about 44% to about by volume of alcohol and about 0.5 to about 2 g of iodine per 100 cc of said test solution.

6. The method of claim 1, comprising the step of:

a) providing a generally light golden-brown test solution containing about 0.5% to about 2.0% iodine, about 48% to about 49.5% water and about 50% alcohol, by volume of said test solution.

7. The method of claim 1, comprising the step of:

a) providing a generally light golden-brown test solution containing about 0.5% to about 2.0% iodine, about 48% to about 49.5% water, about 44% to about 50% alcohol, and about up to 6% hydrogen peroxide, by volume of said test solution.

8. The method of claim 1, comprising the step of:

a) further waiting for a predetermined time period after comparing the color of said area of said paper currency with a predetermined standard;
b) whereby the net result will be substantial dissipation of color on said area of said paper currency to be tested in a genuine paper currency and for a counterfeit paper currency there will no change in the black coloration.

9. A method of detecting counterfeit paper currency by detecting the starch content therein in excess of the genuine currency, comprising the steps of:

(a) providing a paper currency to be tested;
(b) providing a light golden-brown test solution including iodine;
(c) applying said test solution to an area of said paper currency;
(d) waiting for a short time period; and
(e) comparing the color of said area of said paper currency with a predetermined standard to determine if a reaction has taken place;
(f) whereby on the application of said test solution to a counterfeit paper currency the net result will be a change in color from light golden-brown to a black coloration and for a genuine paper currency there will be no immediate change in its light golden-brown coloration.

10. The method of claim 9, comprising the step of:

a) providing a test solution containing iodine and hydrogen peroxide.

11. The method of claim 9, comprising the step of:

a) providing a test solution containing iodine and a solvent selected from the group consisting of alcohol, carbon disulfide, chloroform, ether, carbon tetrachloride, glycerol and an alkaline iodine solution.

12. The method of claim 9, comprising the step of:

a) providing a test solution containing iodine, an iodide selected from the group consisting of sodium iodide and potassium iodide, and alcohol.

13. The method of claim 9, comprising the step of:

a) providing a test solution containing about 44% to about 50% by volume of alcohol and about 0.5 to about 2 g of iodine per 100 cc of said test solution.

14. The method of claim 9, comprising the step of:

a) providing a test solution containing about 0.5% to about 2.0% iodine, about 48% to about 49.5% water and about 50% alcohol, by volume of said test solution.

15. The method of claim 9, comprising the step of:

a) providing a test solution containing about 0.5% to about 2.0% iodine, about 48% to about 49.5% water, about 44% to about 50% alcohol, and about up to 6% hydrogen peroxide, by volume of said test solution.

16. The method of claim 9, comprising the step of:

a) further waiting for a predetermined time period after comparing the color of said area of said paper currency with a predetermined standard;
b) whereby the net result will be substantial dissipation of light golden-brown color on said area of said paper currency to be tested in a genuine paper currency and for a counterfeit paper currency there will no change in the black coloration.

* * * * *